United States Patent
Spillman, Jr. et al.

(10) Patent No.: US 6,206,835 B1
(45) Date of Patent: Mar. 27, 2001

(54) REMOTELY INTERROGATED DIAGNOSTIC IMPLANT DEVICE WITH ELECTRICALLY PASSIVE SENSOR

(75) Inventors: William B. Spillman, Jr., Charlotte, VT (US); Eric M. Weissman, Chagrin Falls; Elmer D. Dickens, Jr., Richfield, both of OH (US)

(73) Assignee: The B. F. Goodrich Company, Brecksville, OH (US)

( * ) Notice: Subject to any disclaimer, the term of this patent is extended or adjusted under 35 U.S.C. 154(b) by 0 days.

(21) Appl. No.: 09/275,308

(22) Filed: Mar. 24, 1999

(51) Int. Cl.⁷ .................... A61B 5/021; A61B 5/0215; A61M 29/00
(52) U.S. Cl. .................. 600/485; 600/481; 606/191; 128/903; 623/900; 623/1
(58) Field of Search .................. 128/903; 600/481, 600/508, 485; 606/191, 198; 623/900, 1

(56) References Cited

U.S. PATENT DOCUMENTS

| | | |
|---|---|---|
| 3,218,638 * | 11/1965 | Honig . |
| 4,026,276 * | 5/1977 | Chubbuck ............... 600/407 |
| 4,114,606 | 9/1978 | Seylar .................... 600/409 |
| 4,227,407 | 10/1980 | Drost . |
| 4,352,960 | 10/1982 | Dormer et al. . |
| 4,361,153 * | 11/1982 | Slocum et al. . |
| 4,453,537 | 6/1984 | Spitzer . |
| 4,528,987 * | 7/1985 | Slocum ................... 128/696 |
| 5,305,758 | 4/1994 | Dietz et al. . |
| 5,306,644 | 4/1994 | Myerholtz et al. . |
| 5,358,514 | 10/1994 | Schulman et al. . |
| 5,372,133 | 12/1994 | Hogen Esch . |
| 5,411,551 | 5/1995 | Winston et al. . |
| 5,620,475 | 4/1997 | Magnusson . |
| 5,626,630 * | 5/1997 | Markowitz et al. . |
| 5,663,507 | 9/1997 | Westervelt et al. . |
| 5,709,225 | 1/1998 | Budgifvars et al. . |
| 5,720,771 | 2/1998 | Snell . |
| 5,735,887 | 4/1998 | Barreras, Sr. et al. . |
| 5,741,315 | 4/1998 | Lee et al. . |
| 5,749,909 | 5/1998 | Schroeppel et al. . |
| 5,807,258 | 9/1998 | Cimochowski et al. . |
| 5,833,603 | 11/1998 | Kovacs et al. . |
| 5,861,019 * | 1/1999 | Sun et al. ................ 607/60 |
| 5,891,180 | 4/1999 | Greeninger et al. . |
| 5,967,986 | 10/1999 | Cimochowski et al. . |
| 5,967,989 | 10/1999 | Cimochowski et al. . |
| 5,972,029 | 10/1999 | Fuisz . |
| 6,015,386 | 1/2000 | Kensey et al. ........... 600/486 |

FOREIGN PATENT DOCUMENTS

| | | | |
|---|---|---|---|
| 9829030 | 7/1998 | (WO) | ........... A61B/5/02 |
| 9942039 | 8/1999 | (WO) . | |
| 9942176 | 8/1999 | (WO) . | |

OTHER PUBLICATIONS

"Sensing and Processing for Smart Structures"; W. B. Spillman, Jr.; Proceedings of the IEEE, vol. 84, No. 1, Jan. 1996 pp. 68–77.

"Bio –Medical Telemetry Sensing and Transmitting Biological Information From Animals and Man"; R. Stuart Mackay; IEEE Press; (e g, pp. 69–70 and pp. 298–315).

* cited by examiner

Primary Examiner—Carl H. Layno
(74) Attorney, Agent, or Firm—Mark D. Saralino; Brian M. Kolkowski

(57) ABSTRACT

An implant device is provided which is responsive to an external interrogation circuit. The implant device includes a structure implantable within a living animal and operatively configured to carry out or assist in carrying out a function within the living animal. The device further includes an electrically passive sensing circuit integral with the structure for sensing a parameter associated with the function. In particular, the sensing circuit includes an inductive element wherein the sensing circuit has a frequency dependent variable impedance loading effect on the interrogation circuit in response to an interrogation signal provided by the exciter/interrogator element, the impedance loading effect varying in relation to the sensed parameter.

19 Claims, 8 Drawing Sheets

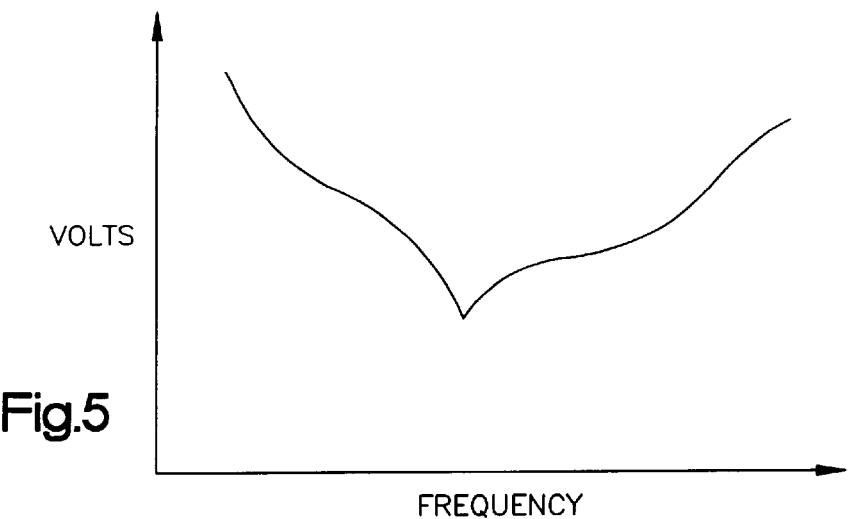
Fig.5
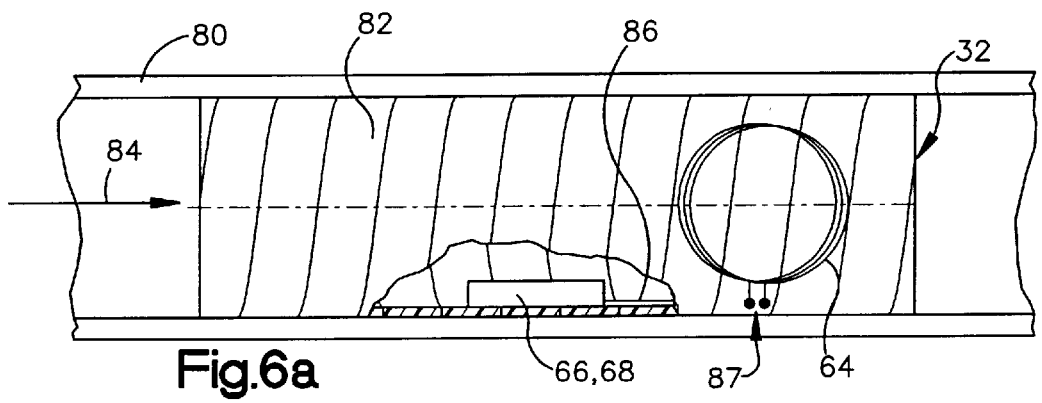
Fig.6a
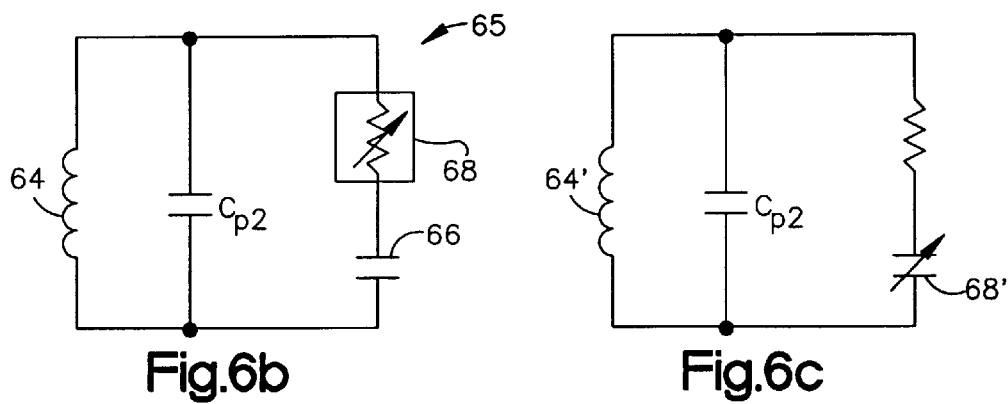
Fig.6b
Fig.6c

REMOTELY INTERROGATED DIAGNOSTIC IMPLANT DEVICE WITH ELECTRICALLY PASSIVE SENSOR

TECHNICAL FIELD

The present invention relates generally to medical implant devices, and more particularly to devices which may be interrogated remotely from outside the body.

BACKGROUND OF THE INVENTION

Various types of medical implant devices have been developed over the years. In many instances, such devices enable humans to live longer, more comfortable lives. Implant devices such as pacemakers, artificial joints, valves, grafts, stents, etc. provide a patient with the opportunity to lead a normal life even in the face of major heart, reconstructive, or other type surgery, for example.

It has been found, however, that the introduction of such implant devices can sometimes lead to complications. For example, the human body may reject the implant device which can ultimately lead to infection or other types of complications. Alternatively, the implant device may malfunction or become inoperative. Therefore, it is desirable to be able to monitor the condition of the implant device. On the other hand, it is highly undesirable to have to perform invasive surgery in order to evaluate the condition of the device.

Still further, it is desirable to be able to monitor conditions related to the use of implant devices. For example, in heart patients it may be helpful to know the amount of blood flowing through a stent or graft in order to evaluate the health of the patient. Again, however, it is undesirable to have to perform invasive surgery in order to evaluate such conditions.

Techniques have been developed which enable the function of an implant device to be monitored remotely from outside the body of the patient. These techniques involve including one or more sensors in the device for sensing the condition of the device. The device further includes a small transceiver for processing the output of the sensors and transmitting a signal based on the output. Such signal typically is a radio frequency signal which is received by a receiver from outside the body of the patient. The receiver then processes the signal in order to monitor the function of the device.

While such conventional techniques may be effective in avoiding the need to perform invasive surgery, there are however several drawbacks associated therewith. For example, the transceiver included in the implant device typically includes complex electrical circuitry such as mixers, amplifiers, microprocessors, etc. for receiving an interrogation signal and for transmitting a response signal based on the output of the sensors. Such complex circuitry has a relatively high cost associated therewith. In addition, the complexity of the circuitry increases the likelihood that the device itself may be defective. This would then require further invasive surgery and could even result in physical harm to the patient.

Still another shortcoming with conventional implant devices with sensors included therein is power concerns. Some type of circuit for providing power to the transceiver is necessary. The circuit may be a built-in power source such as a battery, or a circuit which derives operating power from an external excitation signal. In either case, again the complexity of the circuit and/or the need to replace the battery periodically adds to the cost of the device and increases the opportunity for failure or defects.

In view of the aforementioned shortcomings associated with conventional implant devices, there is a strong need in the art for a medical implant device which can be remotely interrogated but which does not require complex electrical circuitry such as mixers, amplifiers, microprocessors, etc. There is a strong need for a medical implant device which carries out a function within a human or other living animal, and can be remotely interrogated simply and reliably. There is a strong need for such an implant device which permits most or all of the sensor circuitry to be embedded directly within the device. Moreover, there is a strong need for a medical implant device which does not rely on batteries or other complex energy conversion circuits in order to operate.

SUMMARY OF THE INVENTION

The present invention is responsive to the aforementioned shortcomings with conventional devices, and is directed towards an implant device to be implanted within a living animal and responsive to an interrogation circuit having an exciter/interrogator element which is located outside the living animal. The implant device includes a structure implantable within the living animal and operatively configured to carry out or assist in carrying out a function within the living animal. The implant device further includes an electrically passive sensing circuit integral with the structure for sensing a parameter associated with the function, the sensing circuit including an inductive element wherein the sensing circuit has a frequency dependent variable impedance loading effect on the interrogation circuit in response to an interrogation signal provided by the exciter/interrogator element, the impedance loading effect varying in relation to the sensed parameter.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

FIG. 5 is a representative graph of primary current (as detected by voltage across a sense resistor) vs. excitation frequency for the circuit of FIG. 4;

FIG. 6a is a partial cut-away side view of a remotely interrogated stent in accordance with a first embodiment of the present invention;

FIGS. 6b and 6c illustrate different equivalent circuits for the stent in accordance with the present invention;

FIG. 7d represents the equivalent circuit of the stent in FIG. 7a;

FIG. 8b is a simplified electrical diagram of the stent shown in FIG. 8a;

FIG. 9b is a simplified electrical diagram of the stent shown in FIG. 9a;

DESCRIPTION OF THE PREFERRED EMBODIMENTS

Figure 1:
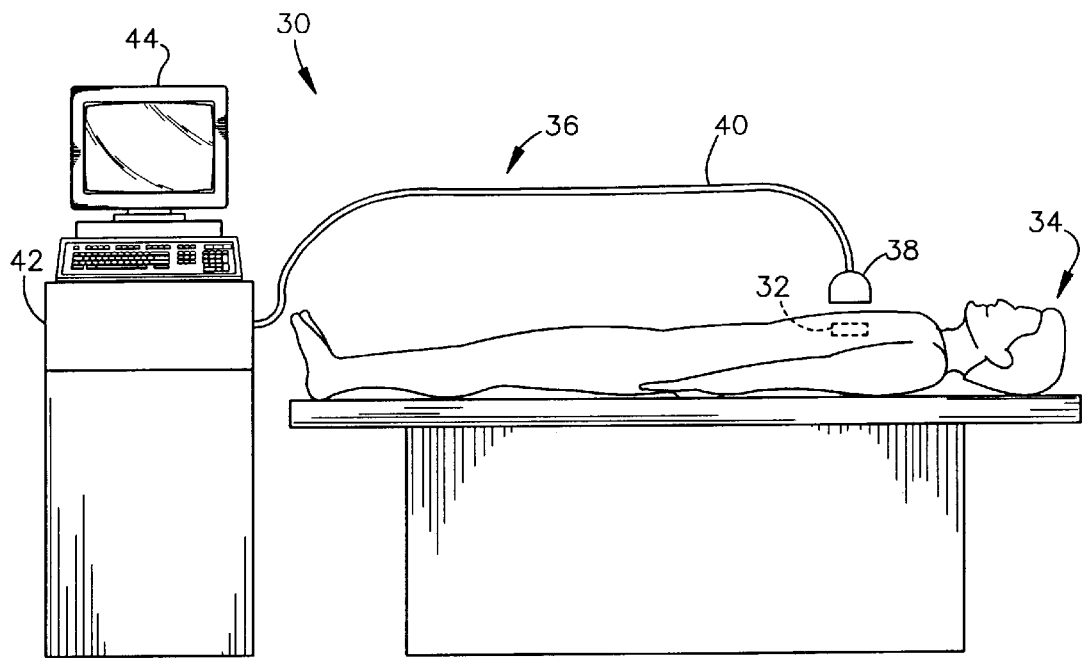
FIG. 1 is an environmental view illustrating a system including a remotely interrogated medical implant device and exciter/interrogator unit in accordance with the present invention.

The present invention will now be described with reference to the drawings, wherein like reference numerals are used to refer to like elements throughout.

Referring initially to FIG. 1, a system for remotely interrogating a medical implant device in accordance with the invention is generally designated 30. The system 30 includes a medical implant device 32 which is implanted in a living animal such as a human patient 34. As is discussed in more detail below, the medical implant device 32 can be any of a wide variety of different types of devices including, for example, a stent, graft, artificial joint, etc.

The device 32 is configured to carry out or assist in carrying out a function within the patient 34. For example, in the case of a stent the device 32 prevents the closing of an arterial wall and permits the flow of blood therethrough. In the case of a graft, the device 32 serves to couple blood flow between two separate ends of an artery. The device 32 may instead consist of an artificial hip or knee which facilitates movement of the leg of the patient 34. Other functions include, but are not limited to, a hemodialysis shunt and spinal brace, for example.

The device 32 includes a sensing circuit (not shown in FIG. 1) which serves to sense a parameter associated with the function performed by the device. For example, in the case of a stent or graft the sensor may be used to detect the degree of restenosis which occurs within the device 32. Alternatively, for example, the sensing circuit may detect an amount of strain or displacement which occurs in an artificial hip or knee. Still further, the sensor may serve to sense the condition of the implant device in carrying out its intended function. For example, in the case of a pacemaker the sensor may detect the pulse rate.

The system 30 further includes interrogation instrumentation 36 for remotely interrogating the implant device 32 in order to evaluate the device function. The instrumentation 36 includes an exciter/interrogator unit 38 which is positioned outside the patient 34 in close proximity to the implant device 32. As will be discussed in more detail below, the exciter/interrogator unit 38 serves to excite the sensing circuit within the device 32. The sensing circuit is designed to have a variable impedance loading effect on the exciter/interrogator unit 38, which varies in relation to the sensed parameter (e.g., blood flow, amount of restenosis, etc.).

The exciter/interrogator unit 38 is coupled via an electrical cable 40 to the main circuitry 42 included in the interrogation instrumentation 36. The main circuitry 42 includes suitable circuits for driving the exciter/interrogator unit 38 as described below, and for processing the output of the exciter/interrogator unit 38 in order to provide an output to an operator (e.g., display 44). In particular, the variable impedance loading effect of the device 32 on the exciter/interrogator unit 38 is detected at different frequencies and processed to produce a display or the like indicative of the function performed using the device 32.

As will be better understood based on the description which follows, the present invention preferably utilizes magnetic coupling between the exciter/interrogator unit 38 and the implant device 32. The sensing circuit in the device 32 is a passive circuit designed to have an impedance loading effect on the exciter/interrogator unit 38. In this manner, the sensing circuit can be a very simple, low cost circuit which is less prone to failure. The device 32 does not require an active transmitter, mixer, amplifier, etc. as in other conventional devices. Moreover, the sensing circuit can be embedded within the device structure to reduce the amount of obstruction which occurs in the device and, for example, to increase performance.

Figure 2:
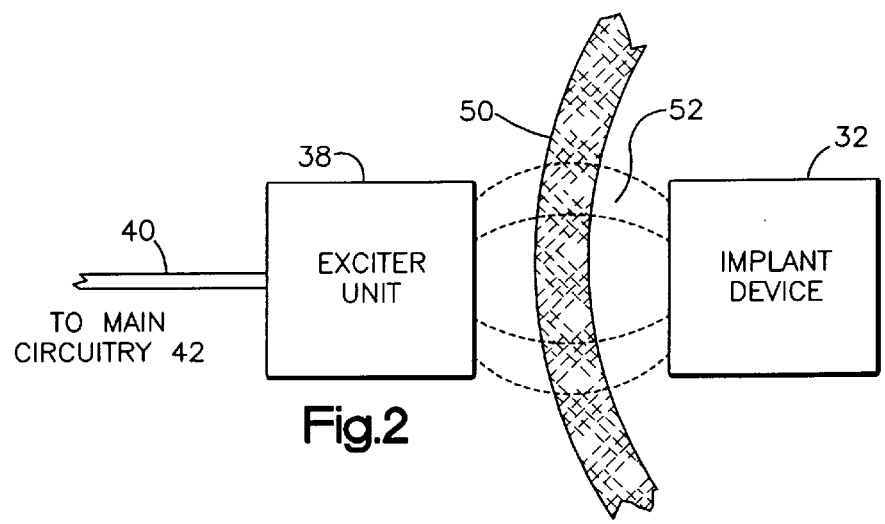
FIG. 2 is a simplified block diagram of the system of FIG. 1.

FIG. 2 represents a simplified block diagram showing the positional relationship between the implant device 32 and the exciter/interrogator unit 38. The exciter/interrogator unit 38 preferably is a hand-held sized device which is held by a doctor, nurse or medical assistant in close proximity to the implant device 32. Since the system 30 is non-invasive, the exciter/interrogator unit 38 may be placed adjacent the implant device 32 with the body of the patient (e.g., skin, muscle tissue, etc.), designated 50, disposed therebetween. The preferred embodiment of the present invention relies on magnetic and/or electromagnetic coupling (represented by field lines 52) between the exciter/interrogator unit 38 and the implant device 32 to interrogate the device 32 non-invasively.

More particularly, the preferred embodiment of the present invention introduces sensor technology developed in the aerospace industry into medical implant devices. Commonly owned U.S. Pat. No. 5,581,248 describes in detail how magnetic coupling between an interrogation circuit and a sensor coil, based on an impedance loading effect, can be used to interrogate an embedded sensor. Heretofore, however, no one has thought to utilize such technology in medical implant devices. The entire disclosure of U.S. Pat. No. 5,581,248 is incorporated herein by reference.

Figure 3:
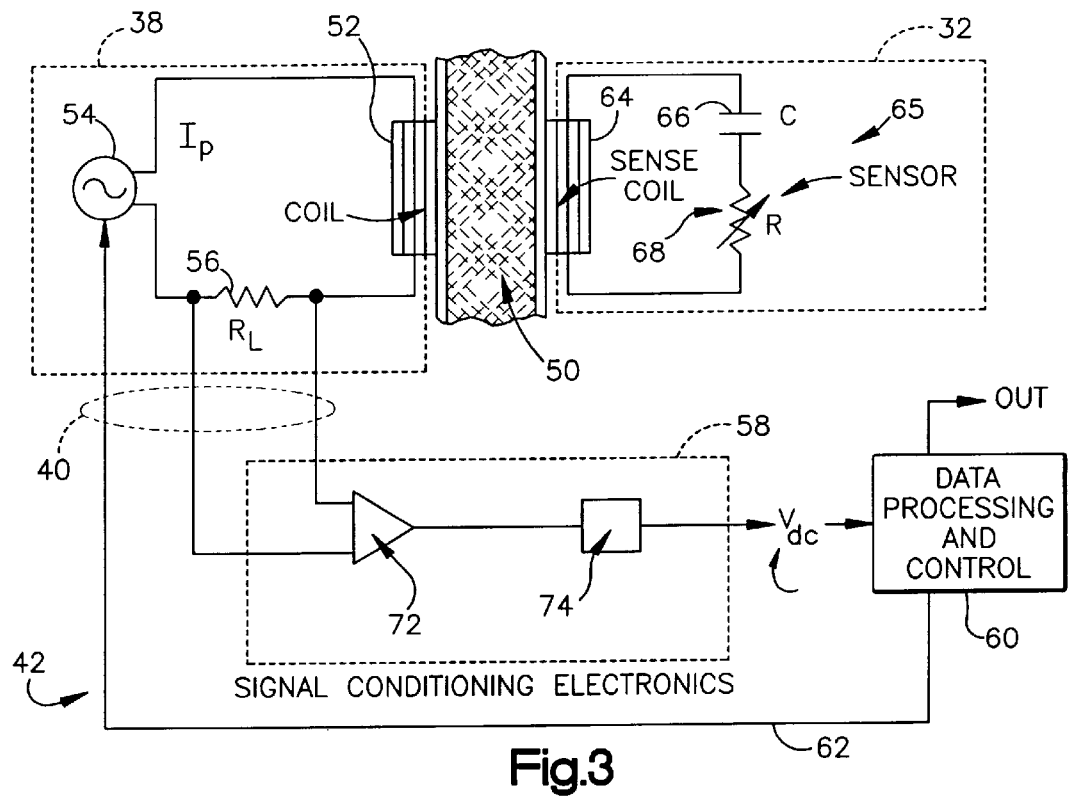
FIG. 3 is a schematic diagram of the system including the remotely interrogated medical implant device and exciter/interrogator unit in accordance with the present invention.

FIG. 3 illustrates the electrical configuration of the exciter/interrogator unit 38 and implant device 32 in more detail. The exciter/interrogator unit 38 includes an exciter/interrogator coil 52, a voltage controlled oscillator 54, and a load sensing resistor 56. The oscillator 54 provides an excitation signal to the exciter/interrogator coil 52 and the load sensing resistor 56 which are coupled in series. The exciter/interrogator unit 38 is coupled via the cable 40 to the main circuitry 42 which includes signal conditioning electronics 58 and a data processing and control section 60. The data processing and control section 60 produces a control signal on line 62 for controlling the frequency and the magnitude of the excitation signal that the oscillator 54 applies to the exciter/interrogator coil 52. The exciter/interrogator coil 52, sensing resistor 56 and oscillator 54 provide a resonant exciter/interrogator circuit that is used to induce currents in a coil within the implant device 32 in order to perform interrogation.

More specifically, the implant device 32 includes a sense coil 64 which is embedded in the structure of the implant device. As is discussed in more detail below in connection with FIGS. 6a, 7a, 8a, etc., the implant device 32 may be any type of implant such as a stent or graft. The sense coil 64 may be integrally secured to a surface of the stent or graft, for example, or even formed directly within the structure. The sense coil 64 is part of a passive resonant sensing circuit 65 which includes, for example, a capacitor 66 and a sensing element 68 in electrical series with the sense coil 64. The sensing element 68 can be any sensor which produces a variable impedance (e.g., resistance, capacitance or inductance), or which produces an output that can be converted into a variable impedance that can change or modulate the impedance of one or more of the resonant circuit components.

As shown in FIG. 3, the sensing element 68 is represented by a variable resistance which varies based on a sensed parameter. In an alternative embodiment, the sensing element 68 may provide a capacitance, inductance and/or resistance which varies based on a sensed parameter. As long as the sensing element 68 in combination with the sense coil 64 alone or together with one or more elements (e.g., capacitor 66) form a resonant sensing circuit 65 (e.g., LC or LRC), the benefits of the invention may be obtained.

The sensing element 68 can be any of a variety of known types of sensors which may be used to sense a functional parameter within the living body. Such parameters may include, but are not limited to, vascular parameters such as blood flow rate, blood pressure, oxygen content, cholesterol, restenosis, glucose level, temperature, etc.; hematology parameters such as blood gases, blood chemistry, hemoglobin content, etc., and skeletal/muscular parameters such as force, strain, displacement, etc. As mentioned above, the sensing element 68 itself may be characterized as an impedance based sensor whose resistance, capacitance and/or inductance varies directly with respect to frequency as a function of the sensed parameter, or another type sensor whose output can be converted into a variable impedance. Exemplary sensor types include electrical, piezoelectric, sonic optical, microfluidic, chemical, membrane, thermal, magnetohydrodynamic, an NMR varient, magnetic, magnetostrictive, biological, microelectromechanical sensors (MEMs), etc.

In the particular examples discussed below, the sensing element 68 may be a MEMs device whose impedance varies as a function of the amount or rate of blood flow through a stent or graft. Alternatively, the sensing element 68 may be a surface acoustic wave (SAW) device which can detect blood flow. In yet another alternative, the sensing element 68 may be a piezoelectric device within a stent or graft for detecting blood pressure.

According to yet another embodiment discussed below, the sensing element 68 may be included within the sense coil 64 itself. For example, the embodiments of FIGS. 7a, 8a, 9a, etc. as described below incorporate the sense coil 64 within the tubular housing of a stent or graft. Changes in the amount of blood flow through the stent or graft and/or the occurrence of restenosis therein affect the overall inductance of the sense coil 64. Hence, the sense coil 64 alone or in combination with one or more other sensing elements 68 may be used to vary the impedance of the resonant sensing circuit based on the sensed parameter.

As is explained more fully in the aforementioned '248 patent, the basic operation of the system 30 of FIG. 3 according to the invention is as follows. The sensing circuit 65 exhibits a resonant frequency which is defined as the frequency which is the point of maximum sensitivity to changes in the excitation current $I_P$ for a given change in the impedance of the sensing element 68. The resonant frequency $f_s$ is determined by the sum total of the reactive elements of the circuit which includes the inductance of the sense coil 64 and the exciter/interrogator coil 52, as well as the capacitance 66 (and parasitic capacitances $C_{P1}$ and $C_{P2}$ shown in FIG. 4) and the value of a coupling constant K. The amplitude of the current through the coil 64 is also a function of the sensing element 68, particularly at the resonant frequency of the sensing circuit 65. When the exciter/interrogator coil 52 has an AC signal applied, current in the primary or exciter/interrogator coil 52 induces current in the secondary or sense coil 64, as in an air gap transformer. This current in the sense coil 64, however, is reflected back to the exciter/interrogator coil 52 by the mutual coupling of the two coils. The sensing resistor 56 is used to detect the current in the exciter/interrogator coil 52.

When the excitation frequency is approximately at the resonant frequency of the sensing circuit 65, the current in the exciter/interrogator coil 52 changes maximally in relation to the value of the sensing element 68. Thus, the condition of the sensing element 68 can be determined as a function of the detected current in the exciter/interrogator coil 52. Using an amplifier 72, the signal conditioning electronics 58 amplifies the voltage developed across the sensing resistor 56 by the exciter/interrogator circuit current $I_P$. This amplified voltage is then rectified and low pass filtered via a rectifier and low pass filter circuit 74 to provide a DC voltage output $V_{dc}$. The control circuit 60 then uses the DC value to determine the state or output of the sensing element 68.

Figure 4:
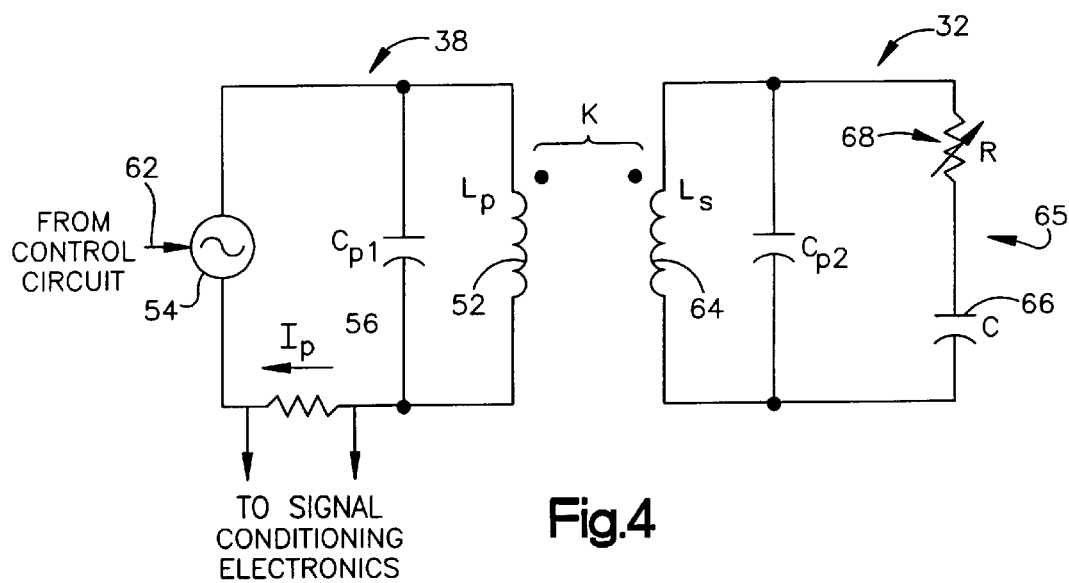
FIG. 4 is a more detailed schematic diagram representing the remotely interrogated medical implant device and exciter/interrogator unit in accordance with the present invention.

FIG. 4 provides a more detailed circuit model of an exciter/interrogator unit 38 and the implant device 32. As shown, the exciter/interrogator unit 38 includes the exciter/interrogator coil 52 that has a determinable inductance $L_P$. The coil 52 and associated components of the exciter/interrogator unit 38 also will exhibit an overall parasitic capacitance, $C_{P1}$, that appears in parallel with the coil inductance. The exciter/interrogator unit 38 further includes the variable frequency oscillator 54 and the sensing resistor 56 used to sense the primary or excitation current $I_P$. Thus, all components in the exciter/interrogator unit 38 are known quantities for each application.

The resonant sensing circuit 65 includes the sense coil 64 which has a determinable inductance, $L_S$, in one embodiment; or in another embodiment an inductance which varies in relation to the sensed parameter. In such embodiment, the sense coil 64 itself forms part of the sensing element 68. The sense coil 64 also has an associated parasitic capacitance, which parasitic capacitance is in effect part of the capacitance $C_{P2}$ which is a discrete capacitor selected to optimize the sensitivity of the device 32 to changes in the value of the sensing element 68. In other words, the value of $C_{P2}$ can be selected, such as based on experimental data for specific circuits, to maximize the current $I_P$ induced in the exciter/interrogator unit 38 as a function of changes in the resistance of the sensing element 68. The sensing circuit 65 also includes the additional discrete capacitor 66 which is selected to adjust the frequency at which the change in current vs. change in sensing element resistance ratio is optimized.

Thus, for the sensing circuit 65, all of the component parameters are known quantities except the coupling constant, K, and the value of the sensing element 68 output. Accounting for the coupling constant K as described more fully in the '248 patent, the DC output of the signal conditioning electronics 58 is indicative of the sensed parameter of the implant device 32.

FIG. 5 is a graph showing in a representative manner a typical frequency response characteristic of the circuit of FIG. 4. By comparing a family of curves determined by monitoring the primary current $I_P$ vs. excitation frequency for different K values (in this example for K=0.1, K=0.5 and K=0.9) and different resistance values for the sensing element 68, the sensed parameter (e.g., blood flow rate, degree of restenosis, etc.) may be determined.

FIG. 6a presents a first embodiment of the present invention in which the medical implant device 32 is a stent. As is known, a stent is a round, spring-like device that provides mechanical support to the wall of a blood vessel such as an artery. As is shown in FIG. 6a, the stent 32 is inserted within a blood vessel 80. The stent 32 is tube shaped structure made up of a generally helical formed wall 82. The stent 32 prevents the walls of the blood vessel 80 from collapsing while providing a path 84 through which blood may flow.

The wall 82 typically is formed of stainless steel or some other material (e.g., a composite and/or plastic material) which is biocompatible within the body. Depending on the embodiment, the wall 82 preferably is made of a non-conductive material or materials in one case, or a conductive material in another case. In this particular embodiment, the wall 82 preferably is made of a non-conductive material such as plastic. The sense coil 64 is formed on an outer (or inner surface) of the tube shaped structure. Alternatively, the sense coil 64 may be embedded within the wall 82. The sense coil 64 is coupled via electrical conductors 86 and one or more through holes 87 to the remainder of the sensing circuit 65 which is formed on an inner surface of the wall structure 82. The sensing element 68 in such an embodiment may be a MEMs device whose capacitance and/or resistance varies as a function of the amount of restenosis which forms on the element 68 within the stent 32. Alternatively, the sensing element 68 may be a piezoelectric device which produces an impedance output which varies as a function of the pressure of the blood flowing within the stent 32. If desirable, the sense coil 64 and all or part of the remainder of the sensing circuit 65 may be covered with a protective coating material to avoid corrosion or other related problems.

Upon being implanted within the vessel 80, the exciter/interrogator unit 38 (FIG. 3) can be positioned outside the body of the patient in close proximity to the stent 32. The exciter/interrogator unit 38 serves to excite the sense coil 64 which in turn induces a current in the load resistor 56 which varies as a result of the variable impedance loading effect of the sensing circuit 65 with respect to frequency. Thus, as the output of the sensing element 68 varies based on the build up of restenosis, change in blood pressure, or other desired parameter, such variation may be detected remotely.

FIG. 6b illustrates the equivalent circuit for the sensing circuit 65 in an embodiment where the sensing element 68 provides a resistance which varies in response to a sensed parameter. FIG. 6c illustrates an equivalent circuit for the sensing circuit 65 in an embodiment where the sensing element 68' produces an output which varies in capacitance based on the sensed parameter. In each case, the impedance loading effect of the sensing circuit 65 varies in accordance with the sensed parameter by virtue of the resonance of the circuit being affected.

Figure 7A:
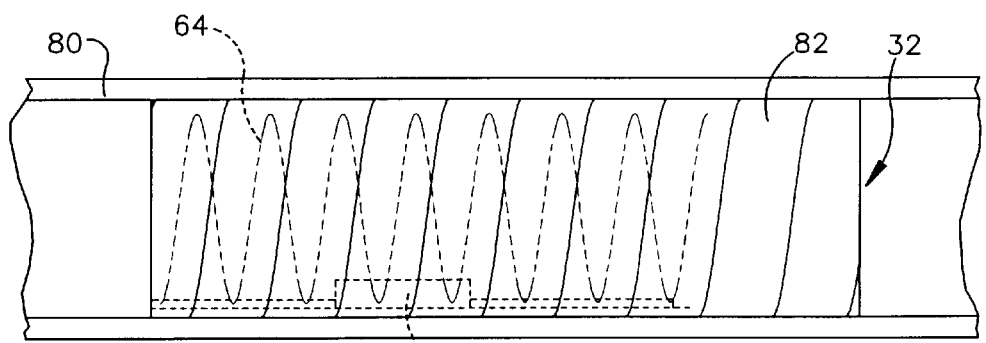
FIG. 7a is a side view of a remotely interrogated stent in accordance with a second embodiment of the present invention.

An alternative embodiment for a stent 32 is shown in FIG. 7a. In this particular embodiment, the helical shaped wall 82 preferably is made of a molded plastic. The sense coil 64 is made up of a conductive wire 92 embedded through several turns in the wall of the helix 82 as shown in cross-section in FIG. 7b. Return wires 94 embedded in and traversing the helix 82 are provided to connect the respective ends of the coil 64 to the remainder of the resonant sensing circuit 65 mounted on the helix 82 as in the previous embodiment. During manufacture, the sense coil 64 may serve as the frame about which the molded plastic helix 82 is formed.

Figure 7B:
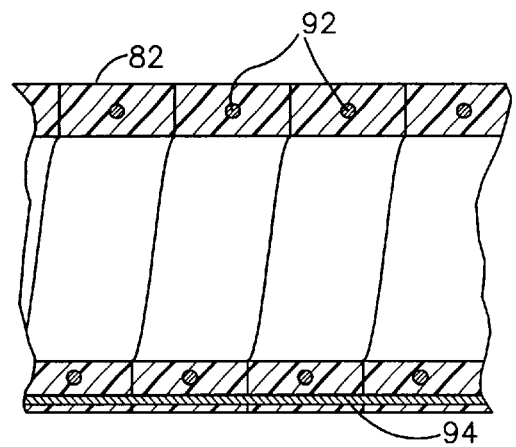
FIGS. 7b and 7c are partial cross-sectional views illustrating possible configurations of the stent in accordance with the present invention.
Figure 7C:
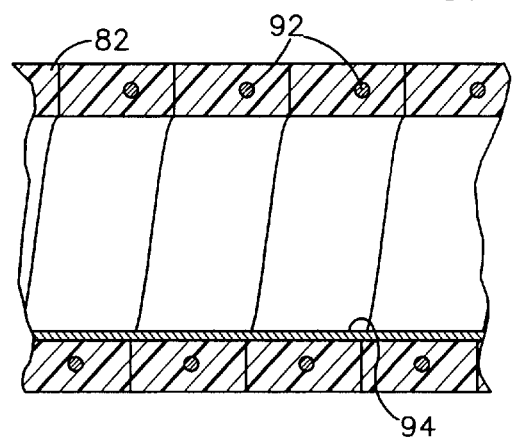

The embodiment of FIG. 7c varies slightly from that shown in FIGS. 7a and 7b. In this particular embodiment, the return wires 94 are formed on the inner surface of the helix 82. Such embodiment simplifies the manufacturing process by allowing the helix 82 to be formed without the return wires 94 traversing the helical turns in an embedded manner.

Figure 7D:
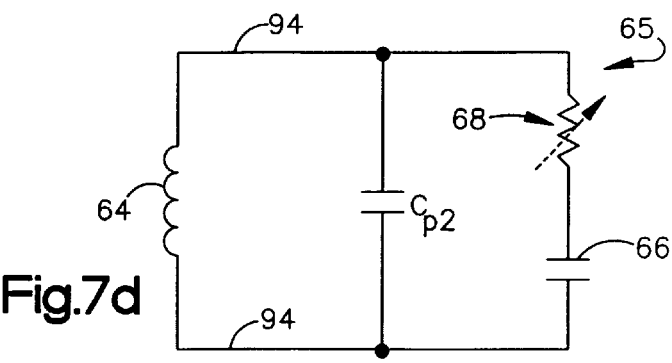

FIG. 7d illustrates generally the equivalent circuit for the stent 32 shown in FIGS. 7a thru 7c. As will be appreciated, the sensing element 68 may be a resistive device as before, or some other type of sensor. In each case, the sense coil 64 provides a means for magnetic coupling between the exciter/interrogator coil 52 and the resonant sensing circuit 65. As blood flow, restenosis, etc. varies within the stent 32, the impact of such variation on the impedance loading effect of the resonant sensing circuit 65 on the exciter/interrogator unit 38 may be detected with respect to frequency. Such information can then be utilized in ascertaining the precise rate of blood flow, degree of restenosis, etc. via the data processing and control 60. As will be appreciated, in each of the embodiments discussed herein the particular type of sensing element 68 will be dictated, of course, by the particular parameter of interest and the manner in which the output of the exciter/interrogator unit 38 is processed.

Figure 8A:
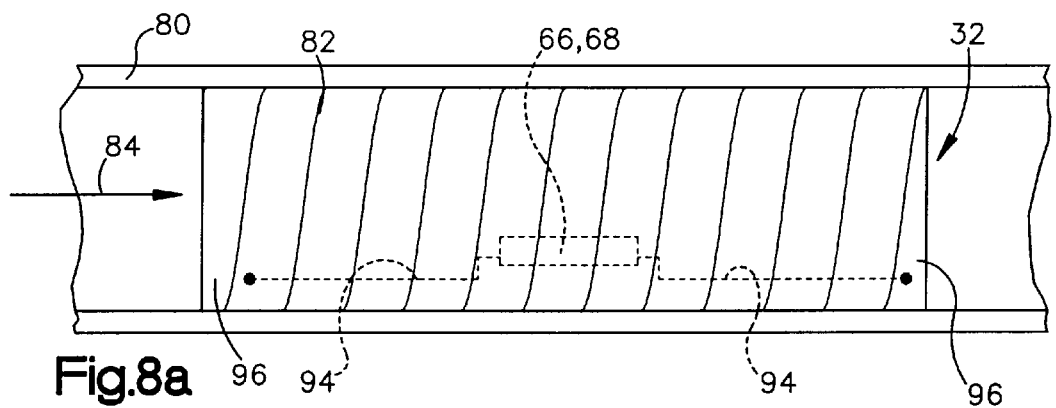
FIG. 8a is a side view of a remotely interrogated stent in accordance with a third embodiment of the present invention.
Figure 8B:
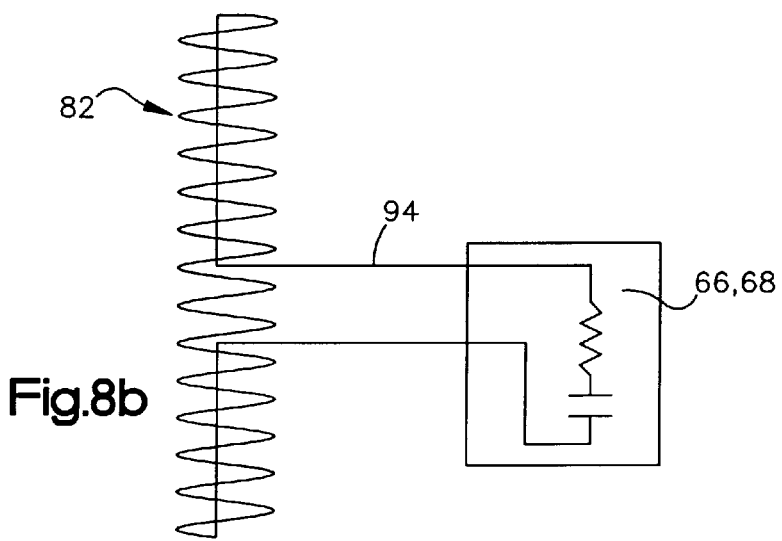

FIG. 8a illustrates another embodiment of a stent 32 which utilizes the conductive properties of a metal-type helix wall 82. The helix wall 82 is made of metal and therefore can itself form the sense coil 64. The metal helix is electrically isolated via a non-conductive coating, for example. Each end 96 of the helix is connected to the remainder of the resonant sensing circuit 65 via return wires 94 as shown in phantom in FIG. 8a. As in the previous embodiments, the resonant sensing circuit with the sensing element 68 may be mounted on the inner surface of the stent 32. FIG. 8b diagrammatically represents the electrical circuit of this particular embodiment.

In each of the embodiments which utilize the body 82 of the stent 32 to form the sense coil 64, e.g., the embodiments of FIGS. 7a, 7c and 8a, it will be appreciated the inductance of the sense coil 64 may itself vary as a function of the sensed parameter. In such instance, the sense coil 64 serves as a sensing element in addition and/or in place a discrete sensing element 68. More particularly, the sense coil 64 formed within the helix may be considered an inductive element. It is combined with a discrete capacitor 66 and resistance 68 to form an LRC resonant sensing circuit 65.

The inductance of the sense coil 64 depends directly on the magnetic permeability of the material inside it. Since iron strongly affects permeability, the amount of blood in the stent 32 as a fraction of the available volume (reduced by restenosis) will modulate the permeability and hence the resonant frequency of the sensing circuit 65. The resonant frequency can be determined by inductively coupling the stent 32 to the exciter/interrogator unit 38 via the externally generated swept frequency magnetic field. Knowledge of the resonant frequency then allows a determination of the inductance of the coil 64. Since the value of inductance depends on the degree of restenosis, an estimate of its occlusion of the stent 32 can be made.

Figure 9A:
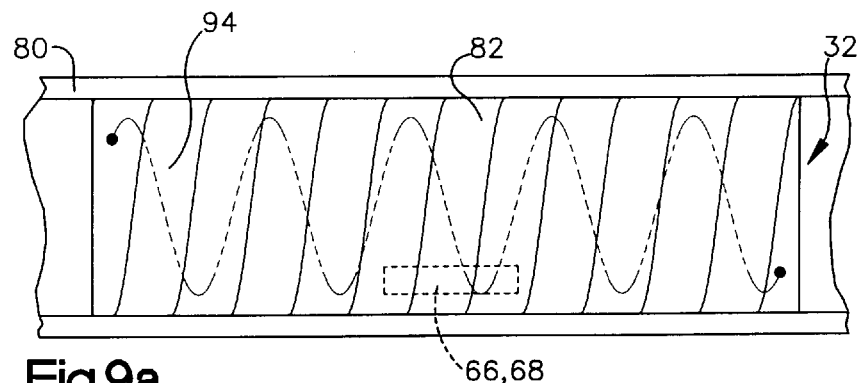
FIG. 9a is a side view of a remotely interrogated stent in accordance with a fourth embodiment of the present invention.
Figure 9B:
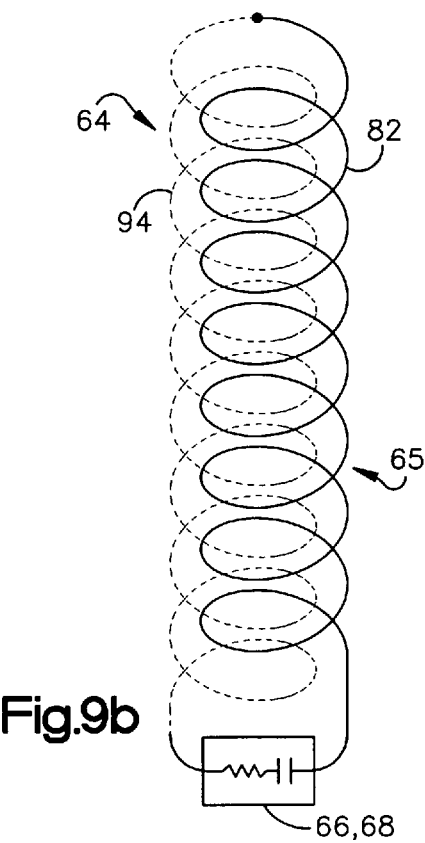

The embodiments of FIGS. 7c and 8a each include some type of direct linear connection via the return wires 94 between the sense coil 64 and the remainder of the resonant sensing circuit 65. Such design may not be optimum from a biocompatibility standpoint or manufacturing standpoint. FIGS. 9a and 9b represent an embodiment which eliminates the need for such return wires 94. In this case, a double helix configuration is used to complete the resonant circuit.

As is shown more clearly in FIG. 9b, the helix wall 82 is made of conductive metal and from one end to the other forms part of the coil 64. The return wire 94 is a second helix with the same pitch as the helix 82 but having an axial direction which is reversed relative to the helix 82. The return wire 94 is connected to one end of the helix 82 and returns to the other end where the resonant sensing circuit 65 can be closed with the capacitance 66 and resistance 68. Electrically, such configuration doubles the inductance L of the coil 64, and currents in the two helical sections 82 and 94 will produce magnetic fields which add rather than cancel. In the presence of a changing magnetic field, conversely, the current in the circuit 65 is doubled.

Other embodiments may include a stent 32 which has a uniform wall rather than a helix shaped wall. In such case, the sense coil 64 may be formed on a surface as in the embodiment of FIG. 6a. Alternatively, the sense coil 64 may be embedded in the structure as in the embodiments of FIGS. 7b and 7c, for example.

Figure 10:
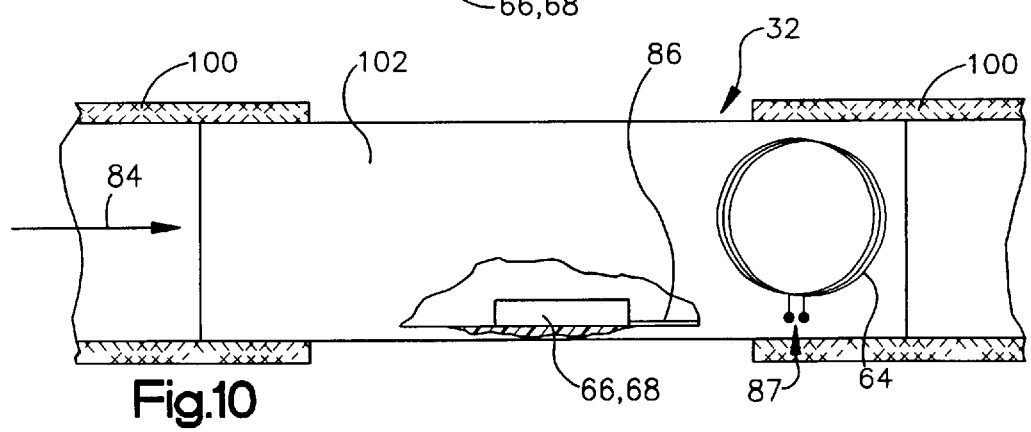
FIG. 10 is a partial cut-away side view of a remotely interrogated graft in accordance with a fifth embodiment of the present invention.

FIG. 10 illustrates an embodiment of the invention wherein the implant device 32 comprises a graft for joining separate ends 100 of a blood vessel. The graft 32 is a tube shaped structure 102 made up of metal such as stainless steel, or a composite and/or plastic material. Using known techniques, the graft 32 is implanted within the patient by securing respective ends 100 of a blood vessel to corresponding ends of the graft 32. Consequently, blood will flow through the interior of the graft 32 as represented by arrow 84.

As in the case of the stent described above, the resonant sensing circuit 65 can be any combination of a sense coil 64, a capacitor 66, a resistor 68, etc. One or more of these components presents an impedance which varies as a function of the parameter to be sensed. Similar to the stent, it is desirable with the graft 32 to sense remotely the degree of restenosis and/or blood flow in the device. By using impedance-based sensing devices, the frequency dependent impedance loading effect of the sensing circuit may be detected externally using the exciter/interrogator unit 38 as previously described.

The embodiment of FIG. 10 is similar to that of FIG. 6a where the sense coil 64 is mounted on a surface of the tube structure 100. The sensing element 68 and capacitor 66, for example, are mounted on an interior surface of the structure 100. Electrical connections to the coil 64 are provided by conductors 86 and vias 87. Operation is fundamentally the same as described above in relation the stent embodiment.

Figure 11A:
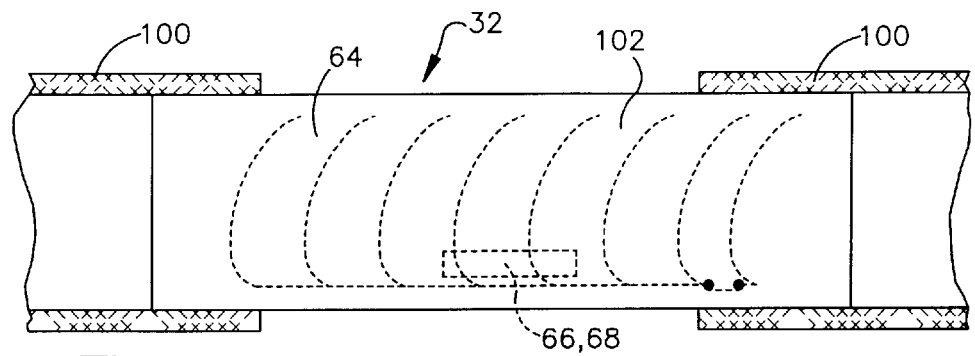
FIG. 11a is a side view of a remotely interrogated graft in accordance with a sixth embodiment of the present invention.
Figure 11B:
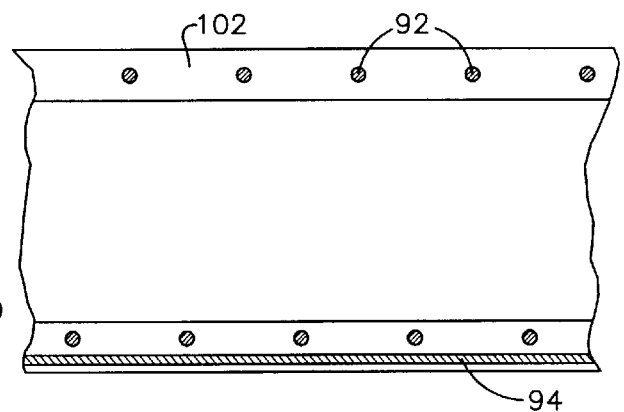
FIGS. 11b and 11c are partial cross-sectional views illustrating possible configurations of the graft in accordance with the present invention.
Figure 11C:
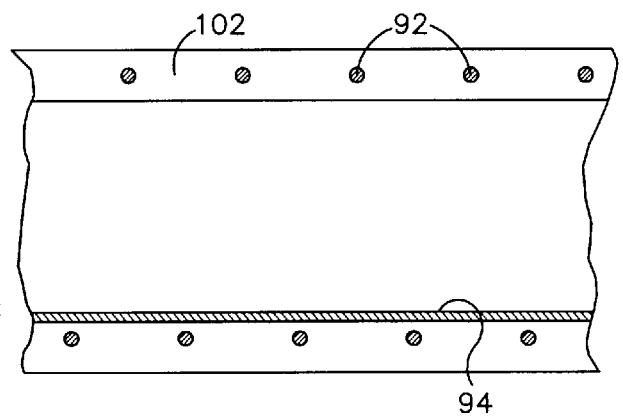

FIGS. 11a thru 11c illustrate an embodiment of a graft 32 analogous to the stent of FIGS. 7a thru 7c. The structure 100 is made of a non-conductive material and the windings of the coil 64 are embedded directly within the tube. Again, for example, the structure 100 may be molded plastic or the like with the coil 64 serving as a skeletal support.

Figure 12:
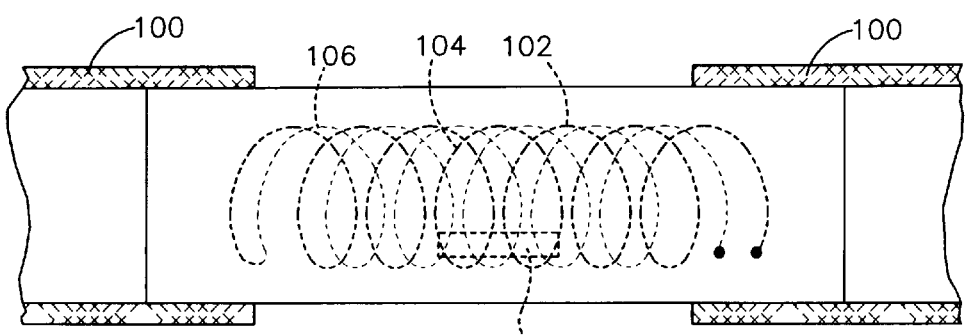
FIG. 12 is a is a side view of a remotely interrogated graft in accordance with a seventh embodiment of the present invention.

FIG. 12 represents an embodiment of a graft 32 which uses a double helix structure similar to the stent in FIG. 9a. In this case, however, since the structure 100 is uniform rather than helical, two separate helical wires 104 and 106 are embedded along the length of the tube 102. Electrically speaking, the circuit is identical to that shown in FIG. 9b. As the amount of blood/restenosis varies in the graft 32, the inductance of the helical wires 104 varies which changes the impedance loading effect on the exciter/interrogator unit 38.

Figure 13:
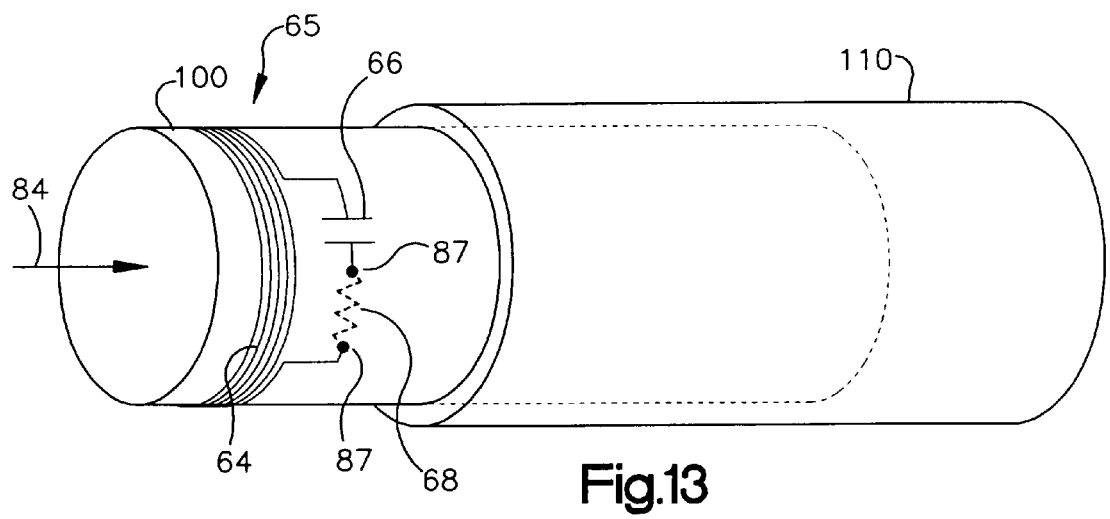
FIG. 13 is a perspective view of a remotely integrated graft in accordance with an eighth embodiment of the present invention.

FIG. 13 illustrates yet another embodiment of a graft 32 (or stent) which is remotely interrogated in accordance with the present invention. In the case of a tube shaped structure 102 serving as the body of the graft or stent, a conventional device may be modified by placing a desired number of windings around the outer surface of the structure 102 to form the sense coil 64. The capacitor 66 or other fixed components may similarly be mounted on the outer surface. The sensing element 68 is mounted on the inside surface and connected through vias 87 to the coil 64 and capacitor 66 to form the LRC resonant sensing circuit 65. Alternatively, the sensing element 68 may be mounted on the outer surface also, provided the sensing element is capable of sensing the desired parameter through the structure 102.

Subsequently, a laminate sheath 110 is applied over the outer surface of the structure 102 and heated to form an integrated graft 32. The sensing circuit 65 can then be interrogated in the same manner described above in connection with the other embodiments.

Although the invention has been shown and described with respect to certain preferred embodiments, it is obvious that equivalents and modifications will occur to others skilled in the art upon the reading and understanding of the specification. For example, various other types of implant devices can benefit from the present invention and the invention is not intended to be limited only to stents and grafts in its broadest application. The present invention includes all such equivalents and modifications, and is limited only by the scope of the following claims.

What is claimed is:

1. An implant device responsive to an interrogation circuit having an exciter/interrogator element which is located outside a living animal, the implant device comprising:

a structure implantable within the living animal and operatively configured to carry out or assist in carrying out a function within the living animal;

an electrically passive sensing circuit integral with the structure for sensing a parameter associated with the function, the sensing circuit including an inductive element wherein the sensing circuit has a frequency dependent variable impedance loading effect on the interrogation circuit in response to an interrogation signal provided by the exciter/interrogator element, the impedance loading effect varying in relation to the sensed parameter.

2. The implant device of claim 1, wherein the structure comprises a composite structure and at least a portion of the sensing circuit is embedded in the composite structure.

3. The implant device of claim 2, wherein the inductive element is embedded in the composite structure.

4. The implant device of claim 1, wherein the interrogation signal is swept in frequency.

5. The implant device of claim 1, wherein the structure is a stent insertable in a blood vessel to facilitate blood flow through the vessel.

6. The implant device of claim 5, wherein the sensing circuit forms an LRC resonant circuit whose resonant frequency is a function of the sensed parameter.

7. The implant device of claim 1, wherein the impedance loading effect of the sensing circuit varies in relation to the sensed parameter as a function of at least one of inductance, capacitance, resistance, resistance and inductance, resistance and capacitance, inductance and capacitance, and inductance, resistance and capacitance.

8. The implant device of claim 1, wherein the inductive element comprises a coil.

9. The implant device of claim 1, wherein the sensing circuit is laminated at least in part to a surface of the structure.

10. An implant device responsive to an interrogation circuit having an exciter/interrogator element which is located outside a living animal, the implant device comprising:

a structure implantable within the living animal and operatively configured to carry out or assist in carrying out a function within the living animal; and an electrically passive sensing circuit integral with the structure for sensing a parameter associated with the function;

wherein the sensing circuit includes an inductive element;

wherein the sensing circuit has a frequency dependent variable impedance loading effect on the interrogation circuit in response to an interrogation signal provided by the exciter/interrogator element, the impedance loading effect varying in relation to the sensed parameter; and wherein the structure is a graft insertable in line with an existing blood vessel for facilitating blood flow through the vessel.

11. The implant device of claim 10, wherein the sensing circuit forms an LRC resonant circuit whose resonant frequency is a function of the sensed parameter.

12. The implant device of claim 10, wherein the graft comprises a composite structure and the inductive element is embedded in the composite structure.

13. The implant device of claim 10, wherein the inductive element is a double helix structure.

14. The implant device of claim 10, wherein the sensed parameter represents a degree of restenosis within the graft.

15. An implant device responsive to an interrogation circuit having an exciter/interrogator element which is located outside a living animal, the implant device comprising:

a structure implantable within the living animal and operatively configured to carry out or assist in carrying out a function within the living animal; and an electrically passive sensing circuit integral with the structure for sensing a parameter associated with the function;

wherein the sensing circuit includes an inductive element;

wherein the sensing circuit has a frequency dependent variable impedance loading effect on the interrogation circuit in response to an interrogation signal provided by the exciter/interrogator element, the impedance loading effect varying in relation to the sensed parameter; and wherein the sensing circuit comprises a SAW sensor having an output dependent upon the sensed parameter to produce changes in the impedance loading effect of the sensing circuit.

16. The implant device of claim 15, wherein the sensing circuit comprises a MEMs sensor having an output dependent upon the sensed parameter to produce changes in the impedance loading effect of the sensing circuit.

17. An implant device responsive to an interrogation circuit having an exciter/interrogator element which is located outside a living animal, the implant device comprising:

a structure implantable within the living animal and operatively configured to carry out or assist in carrying out a function within the living animal; and an electrically passive sensing circuit integral with the structure for sensing a parameter associated with the function;

wherein the sensing circuit includes an inductive element;

wherein the sensing circuit has a frequency dependent variable impedance loading effect on the interrogation circuit in response to an interrogation signal provided by the exciter/interrogator element, the impedance loading effect varying in relation to the sensed parameter:

wherein the structure is a stent insertable in a blood vessel to facilitate blood flow through the vessel; and wherein the stent comprises a composite structure and the inductive element is embedded in the composite structure.

18. An implant device responsive to an interrogation circuit having an exciter/interrogator element which is located outside a living animal, the implant device comprising:

a structure implantable within the living animal and operatively configured to carry out or assist in carrying out a function within the living animal; and an electrically passive sensing circuit integral with the structure for sensing a parameter associated with the function;

wherein the sensing circuit includes an inductive element;

wherein the sensing circuit has a frequency dependent variable impedance loading effect on the interrogation circuit in response to an interrogation signal provided by the exciter/interrogator element, the impedance loading effect varying in relation to the sensed parameter;

wherein the structure is a stent insertable in a blood vessel to facilitate blood flow through the vessel; and wherein the inductive element is a double helix structure.

19. An implant device responsive to an interrogation circuit having an exciter/interrogator element which is located outside a living animal, the implant device comprising:

a structure implantable within the living animal and operatively configured to carry out or assist in carrying out a function within the living animal;

an electrically passive sensing circuit integral with the structure for sensing a parameter associated with the function;

wherein the sensing circuit including an inductive element;

wherein the sensing circuit has a frequency dependent variable impedance loading effect on the interrogation circuit in response to an interrogation signal provided by the exciter/interrogator element, the impedance loading effect varying in relation to the sensed parameter;

wherein the structure is a stent insertable in a blood vessel to facilitate blood flow through the vessel; and wherein the sensed parameter represents a degree of restenosis within the stent.

* * * * *